United States Patent [19]
Tilton, Jr.

[11] Patent Number: 5,766,157
[45] Date of Patent: Jun. 16, 1998

[54] INSTRUMENTATION FOR SURGICAL ENDOSCOPIC INSERTION AND APPLICATION OF LIQUID AND GEL MATERIAL

[76] Inventor: Eugene B. Tilton, Jr., 513 Dorrington Blvd., Metairie, La. 70005

[21] Appl. No.: 644,504

[22] Filed: May 10, 1996

Related U.S. Application Data

[63] Continuation-in-part of Ser. No. 625,098, Apr. 1, 1996, which is a continuation-in-part of Ser. No. 407,409, Mar. 17, 1995, Pat. No. 5,503,623.

[51] Int. Cl.$^6$ .......................... A61B 17/00; A61M 5/00
[52] U.S. Cl. .......................... 604/264; 604/261; 604/13; 604/15; 606/151; 606/1
[58] Field of Search .......................... 128/750, 200.14, 128/200.18, 200.19; 601/160–163, 166, 169; 604/27, 28, 36, 39, 43–45, 48, 49, 51, 93, 94, 181, 187, 239, 261, 264

[56] References Cited

U.S. PATENT DOCUMENTS

| | | | |
|---|---|---|---|
| 5,257,973 | 11/1993 | Villasuso | 604/49 |
| 5,263,927 | 11/1993 | Shlain | 604/13 |
| 5,295,952 | 3/1994 | Pietrafitta | 604/15 |
| 5,304,187 | 4/1994 | Green et al. | 604/13 X |
| 5,310,407 | 5/1994 | Casale | 604/59 |

*Primary Examiner*—Jennifer Bahr
*Assistant Examiner*—Stephen Huang
*Attorney, Agent, or Firm*—Pravel, Hewitt, Kimball & Krieger

[57] ABSTRACT

A method and apparatus for laparoscopic insertion and application of a liquid, gel or like medicinal material enables the laparoscopic surgeon to utilize various spray patterns to apply the desired material. In laparoscopy surgery of the abdomen (including pelvis), all instrumentation and all surgical products must be introduced through "ports" consisting of valved, sleeved or tubes. To properly and efficiently introduce and apply liquid, gel or like medicinal material, the present invention provides a method and apparatus for dispensing the desired material with a desired pattern or spray. The instrument consists of an elongated instrument body that can receive a selected flexible delivery tube having a distal end with a nozzle. The instrument body articulates at its distal end, thereby flexing the dispensing tube. The selected nozzle of the selected dispensing tube can be flexed to dispense with a desired spray pattern into any position of the patient's abdominal cavity.

20 Claims, 10 Drawing Sheets

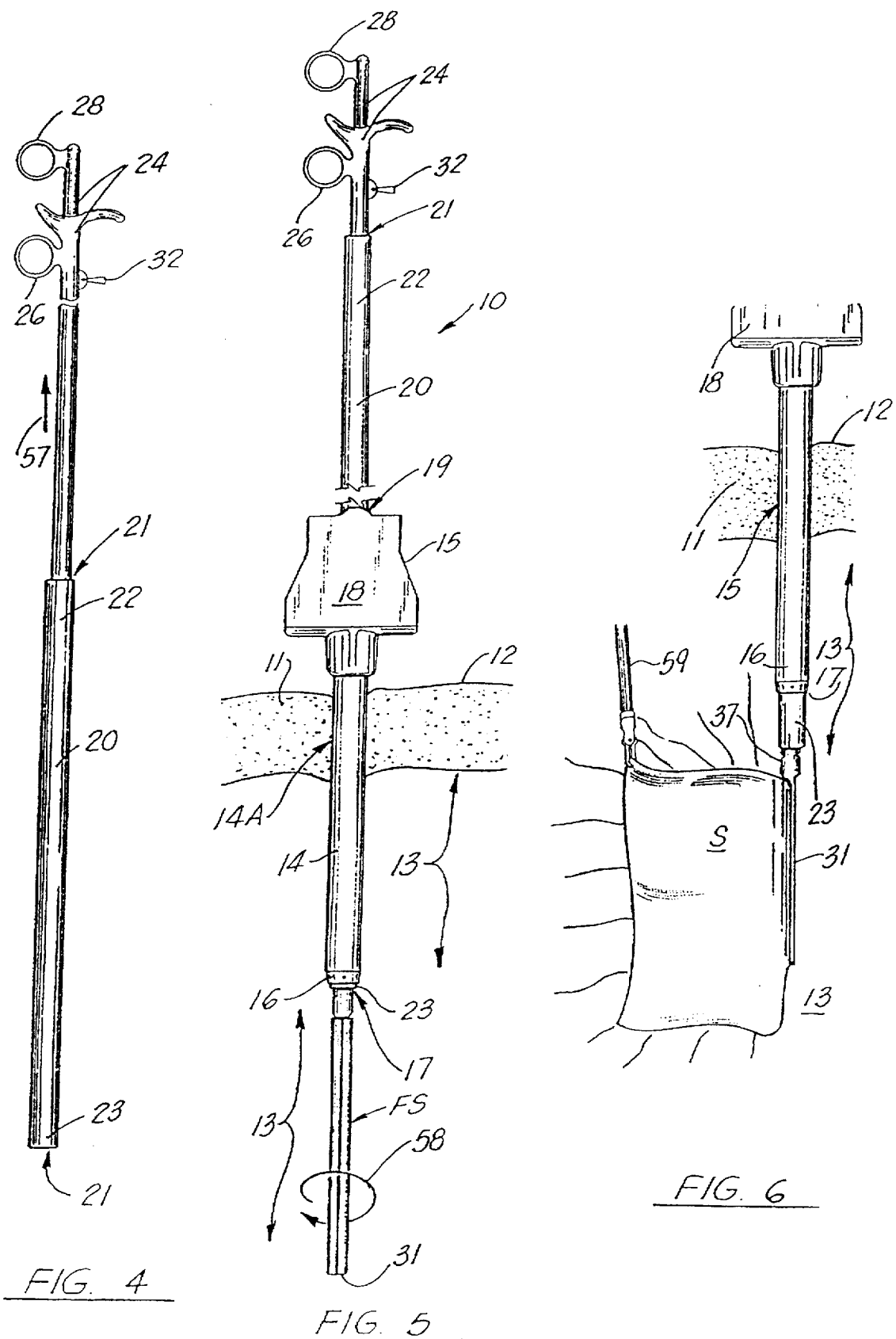

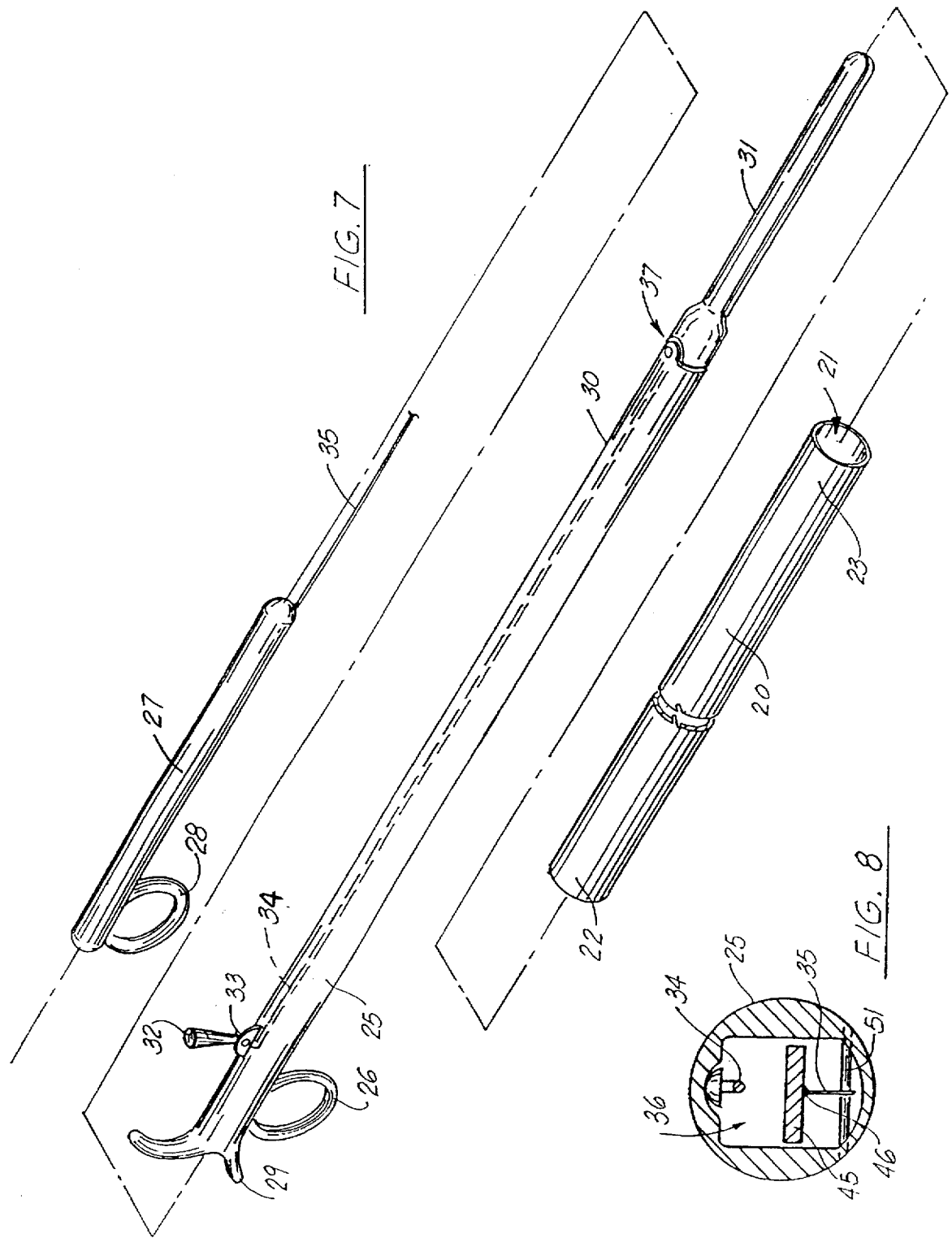

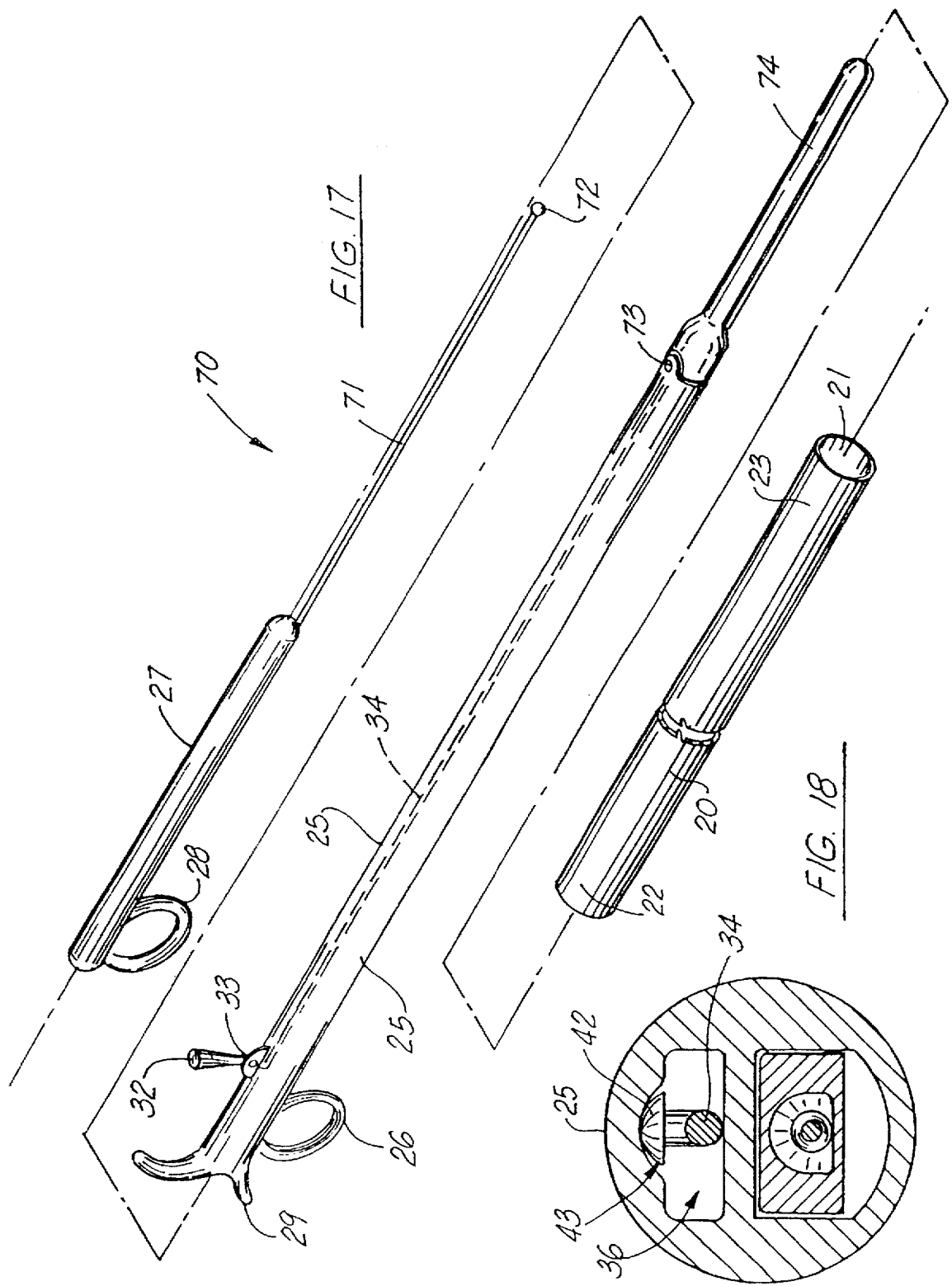

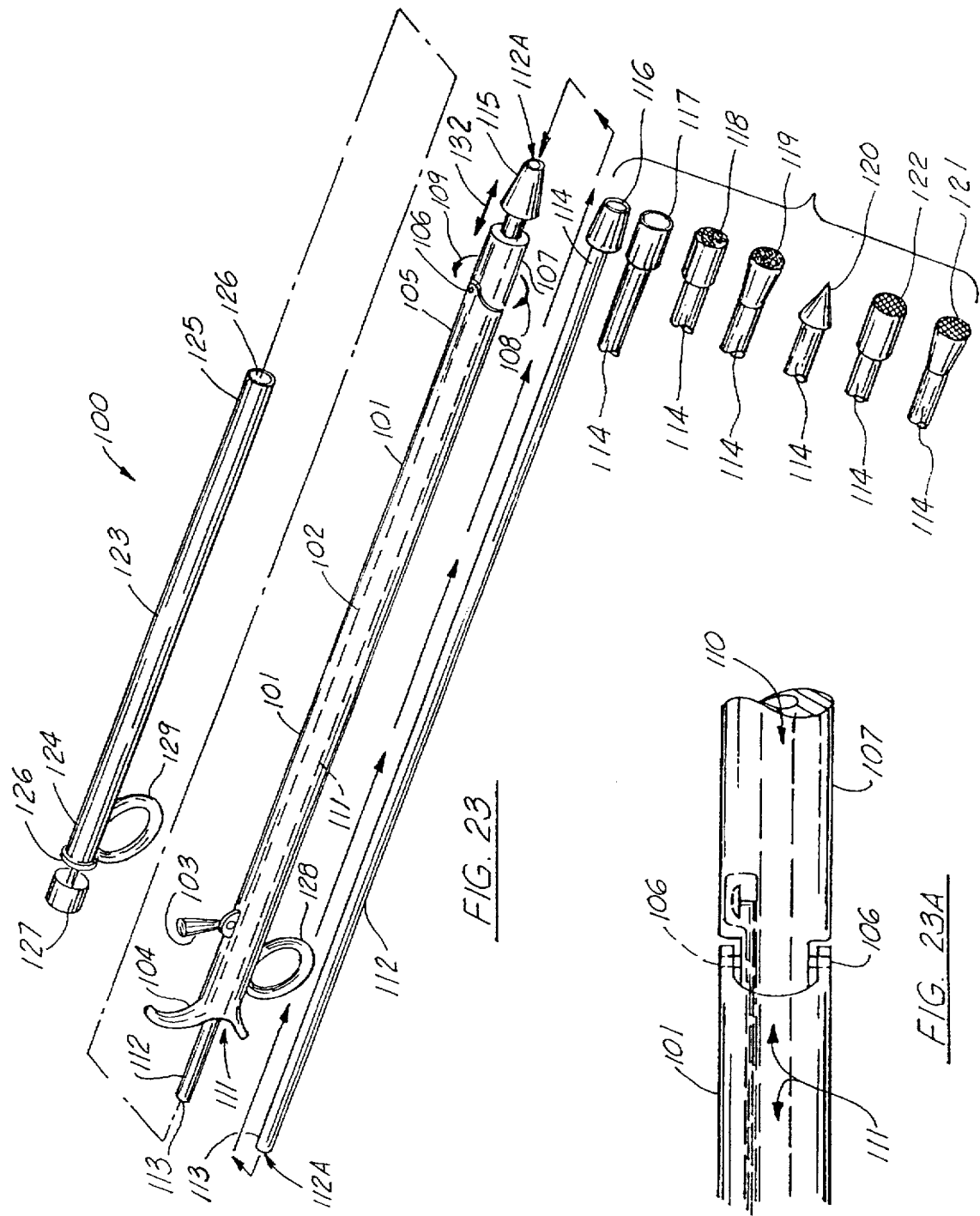

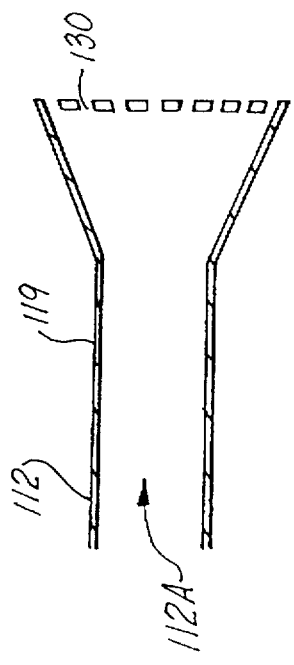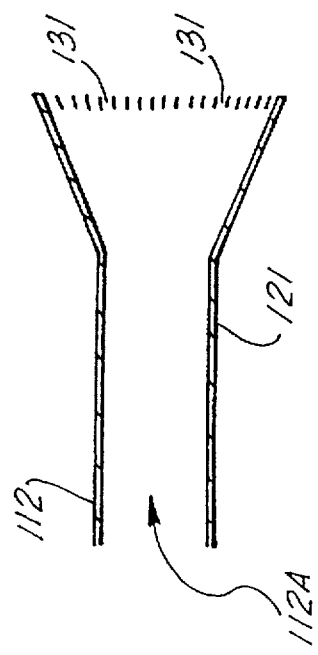

INSTRUMENTATION FOR SURGICAL ENDOSCOPIC INSERTION AND APPLICATION OF LIQUID AND GEL MATERIAL

CROSS REFERENCE TO RELATED APPLICATIONS

This is a continuation-in-part of U.S. patent application Ser. No. 08/625,098, filed Apr. 1, 1996, which is a continuation-in-part of U.S. patent application Ser. No. 08/407,409, filed Mar. 17, 1995 (now U.S. Pat. No. 5,503,623) which is incorporated herein by reference.

BACKGROUND OF THE INVENTION

1. Field of the Invention

The present invention relates to a method and apparatus for laparoscopic introduction and application of liquid, gel, and like medicinal materials.

2. General Background

Surgery performed within the pelvis and abdomen by means of laparoscopy utilizes of one or more entry "ports" in varying size. The majority of sizes is in the range of five (5) millimeters to fifteen (15) millimeters. Each port consists of a tube with proximal and distal ends. A valve structure on the proximal end of the port member allows instruments to be passed through the abdominal wall while maintaining appropriate intra-abdominal $CO_2$ pressure.

While instruments pass easily through the associated port member and its valve structure, liquids, gels, and like medicinal materials cannot be easily administered in laparoscopic surgery.

In laparoscopy surgery, there are or will be a variety of liquid, gel and like medicinal materials that require application in the abdomen (including the pelvis). Because these products have specific medical purposes (examples: adhesion prevention and as a delivery vehicle) the application will have to be precise (to targeted areas or tissues) as opposed to the general way irrigating solutions are administered to wash or rinse tissues during surgery. Also, because these products will be expensive they cannot be wasted and precise application is desired.

Currently, liquids or solutions are usually administered through a common laparoscopy instrument called a suction/irrigator, aspiration/irrigator, irrigator, irrigating cannula, cannula or other similar terminology. These are simple straight tubes usually ranging from between about 3 mm and 5 mm in diameter with an opening on the distal end and possibly some holes on the side of the tube near that end.

Rinsing or irrigating fluids are flushed in to wash and moisten tissues. These simple tubes (usually metal or plastic) can also administer some liquid medical products though but not with precision or purpose and not in any specific, selected direction or specific, selected pattern. There are also long needles used for injection of medicines or retrieving of eggs from ovaries. However, these are simply an extension of the well-known standard injection needle. Such needles are for injection of liquid and medicines into tissues while the present invention is for applying liquid, gels and like medicinal materials onto the surface of tissues even if these products attach to or ultimately penetrate into the tissues.

SUMMARY OF THE INVENTION

The present invention is designed for a variety of installation requirements and a variety of products. There are a variety of head designs to effect the type of delivery or delivery pattern and pass different product variations. Some of the heads have variously narrowing conical shapes and are designed for gels, liquids and medicines that need application to certain size local spots. Other heads for dispersion of gels only, enhanced by a combination of shape (straight and widening conical) and the presence of grids. A wide (but not haphazard, wasteful, or harmful) distribution is desired.

In a conical head, the grids can be angled outwardly to further cause the gel to disperse more outward to cover even more area when desired. Some of the heads have multiple holes at the end. These are for controlled dispersion of liquids only, with two preferred shapes: straight and widening conical. The conical shape is also for wider dispersion. The holes can also be angled outwardly to cause the liquid to disperse in a wider pattern. These various heads are uniquely designed for particular applications and for various products. The various heads and their associated long flexible portion are all designed to be interchangeable and fit into the main body of the instrument.

The distal end of the main body of the instrument can be angled up to 90 degrees in two pivotal directions. When the instrument is manually rotated, this allows aiming of the selected delivery head in virtually any direction to reach any area in the abdomen (including pelvis). This also includes hard to reach areas such as parts of the intestines, the under side of the uterus, behind the ovaries and the entire anterior abdominal wall.

To further reach difficult areas, the inner portion of the main body can be pushed in to move the flexible plastic tube and its applicator head farther into the abdomen to small areas, more distant areas or, most importantly, areas that couldn't otherwise be reached because the main body of the instrument is blocked by other tissues or organs.

The instrument overall diameter can vary, probably between about 5 mm and 15 mm with approximately 10 mm being a preferred general size.

The present invention thus provides a method and apparatus for laparoscopic introduction and application of a variety of liquid, gel, and medicinal materials, enabling the surgeon to more efficiently use these materials. In laparoscopy surgery of the abdomen (including pelvis), all instrumentation and all surgical products must be introduced through "ports" consisting of valved sleeves or tubes. To properly and more efficiently introduce and apply a variety of liquids, gels and medicines (such as Sepracoat, Sepragel and Flo-Gel), the present invention provides a method and apparatus for dispensing these products through a flexible tube which can be angled and adjusted to guide them to any site, including hard to reach areas.

Interchangeable tubes allow having a variety of heads for different types of dispersement of the liquid, gel, or medicine (examples: pin-point application, broad application, shower-like spray application).

The present invention provides an improved method and apparatus for dispensing liquid medicinal, gel, or like material into a patient's abdomen during a laparoscopy procedure. The method includes the surgical forming of a small opening through the patient's abdominal wall. A first tubular member is placed through this surgical opening, the tubular member having proximal and distal end portions. The second tubular member is then inserted into the bore of the first tubular member and through a valve structure that can be provided if desired on the proximal end of the first tubular member. This allows the surgeon to valve the flow of gases between the patient's abdominal and the proximal end of the first tubular member. The second tubular member defines an instrument body that can be extended into the patient's abdominal cavity. The surgeon selects a flexible dispensing tube and places it in the bore of the second tubular member or instrument body. This flexible dispensing tube has a distal end with a nozzle for applying a desired liquid, gel or medicinal material to the patient's abdominal cavity with a desired spray pattern. In the preferred method, there are a plurality of different flexible dispensing tubes, each having a different spray pattern that can be created by differing the number of holes through each nozzle in the direction of orientation of the holes. Thus, the holes can be in the form of small channels with central longitudinal axes that are angled relative to the central longitudinal axis of the flexible dispensing tube.

The apparatus of the present invention provides a laparoscopy instrument that comprises a first laparoscopy tube that can be placed surgically by a surgeon through an opening in the patient's abdominal wall, the first tube having a bore. An instrument body is provided that can be placed into the bore of the laparoscopy tube. The instrument body has proximal and distal end portions and an instrument body bore.

One or more flexible dispensing tubes are provided that each has a proximal and distal end. The tube is preferably sized and shaped to fit the instrument body bore and is flexible at least at the distal end portion thereof. In the preferred embodiment, each of the flexible dispensing tubes is in an elongated cylindrically shaped hollow tube of silicone, rubber, or rubber-like material. A nozzle is provided at the distal end of each of the dispensing tubes for dispensing liquids, gels and like medicinal materials into the patient's abdominal cavity.

Handles are provided on the instrument body for manipulating the distal end of the instrument body so that a contained flexible dispensing end portion of the dispensing tube can be moved in a sliding fashion. Further, a lever operates a pushrod to flex or pivot the distal end of the instrument body and the contained dispensing tube. This allows a wide range of positions for placement of the nozzle within the patient's abdominal cavity. The hollow bore of each of the dispensing tubes allows the transmission of fluid, gel, liquid, and like medicinal material between the proximal and distal end portions of the dispensing tube when the tube occupies the bore of the instrument body and the nozzle is positioned at a desired location with in the patient's abdominal cavity.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 4 is a side view of the preferred embodiment of the apparatus of the present invention showing the inserter instrument with a sheet of surgical material loaded in the distal end portion of the inserter instrument body;

FIG. 5 is a schematic view illustrating placement of the apparatus of the present invention through a patient's abdominal wall and illustrating the method of the present invention;

FIG. 6 is a side schematic view illustrating the method of the present invention;

FIG. 7 is an exploded perspective view of the preferred embodiment of the apparatus of the present invention;

FIG. 8 is a sectional view of the preferred embodiment of the apparatus of the present invention;

FIG. 17 is a perspective exploded view of a second alternate embodiment of the apparatus of the present invention;

FIG. 18 is a transverse cross-sectional view of the embodiment of FIG. 17;

FIG. 23 is a perspective exploded view of a fifth embodiment of the apparatus of the present invention;

FIG. 23A is a fragmentary section view of the fifth embodiment of FIG. 23; and

FIGS. 24–25 are fragmentary sectional views of two of the head portions of the fourth embodiment of the apparatus of the present invention.

DETAILED DESCRIPTION OF THE PREFERRED EMBODIMENT

Figure 1:
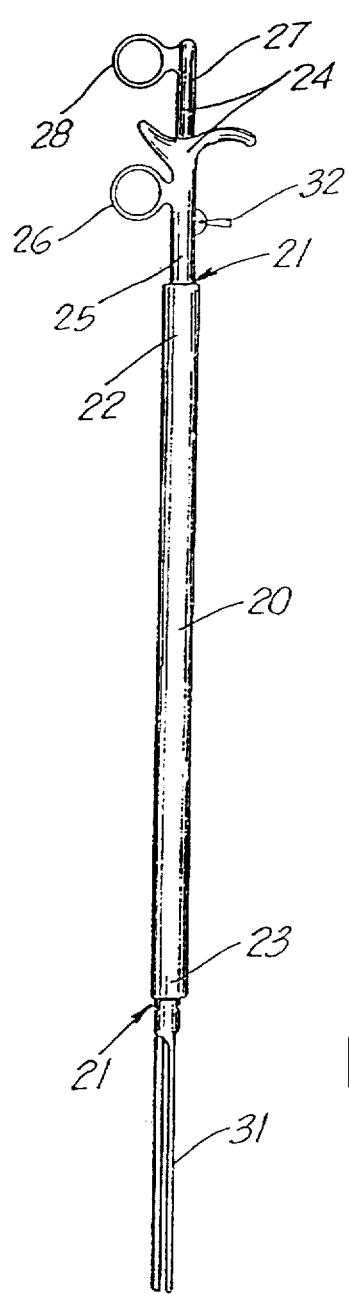
FIG. 1 is a side view of the preferred embodiment of the apparatus of the present invention.

FIGS. 1–6 illustrate the preferred embodiment of the apparatus of the present invention designated generally by the the numeral 10. Laparoscopy instrument 10 includes an elongated structure that can be placed through the abdominal wall 11 of a patient as shown in FIG. 5. Also shown in FIGS. 5 and 6 is the patient's skin 12 and the abdominal cavity 13 into which an inserter instrument portion 24 of the instrument 10 will be placed.

Tubular port 14 extends through an opening 14A formed with the tubular member 14 through the patient's abdominal wall 11. This procedure of placing a port in the abdominal wall 11 is per se known. In such a procedure, it is known in the art to inflate the abdomen to give the surgeon a better view of the surgical site. The tubular port 14 is a commercially available structure that includes a proximal end 15 and a distal end 16. The tubular port 14 provides an elongated open end cylindrical bore 17 so that the surgeon can communicate between the abdominal cavity 13 and the exterior of the patient. Cylindrical bore 17 is valved with valving member 18. The valving member 18 likewise provides a bore that is in communication with the cylindrical bore 17. Such a port 14 with its valving member 18 is sold commercially for use in laparoscopic surgery.

An elongated inserter tube member 20 is sized and shaped to fit the internal bore 17 of the tubular port 14. The tubular member 20 provides a generally cylindrical outer surface that is of an external diameter that is substantially the same as or slightly smaller than the internal diameter cylindrical bore 17. The bore 19 of valving member 18 is also generally cylindrically shaped to conform to the outer surface of tubular member 20. The inserter tube member 20 has a proximal end 22 and a distal end 23. The tubular member 20 has a uniform cylindrical bore 21 that is open ended.

An elongated inserter instrument 24 is comprised of external tubular member 25 and internal tubular member 27 (see FIG. 7). The external tubular member 25 has a handle 26 for manipulating it. Similarly, the internal tubular member 27 has a handle 28. The two handles 26, 28 are each in the form of a ring so that the surgeon can place one of his or her fingers through the handles 26, 28 for manipulating and sliding the member 27 relative to the member 25.

Figure 10:
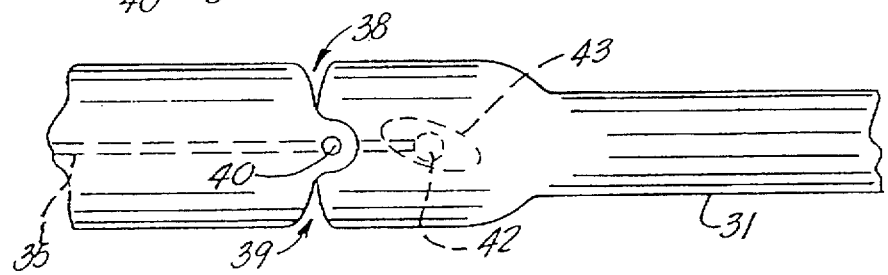
FIG. 10 is a top partial view of the preferred embodiment of the apparatus of the present invention.
Figure 11:
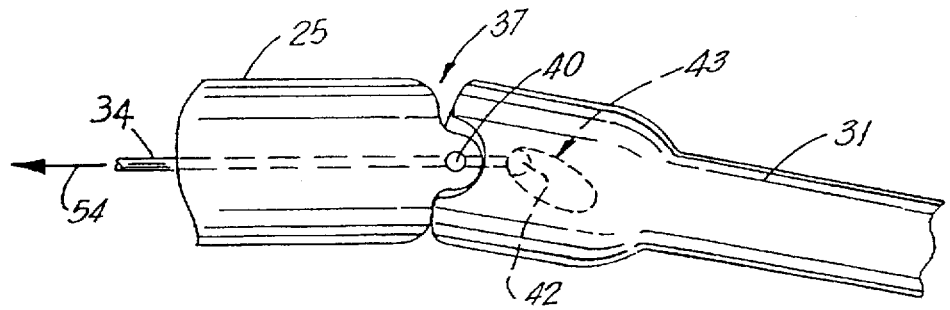
FIG. 11 is a top partial view of the preferred embodiment of the apparatus of the present invention illustrating an articulation of the distal end portion of the inserter instrument body.
Figure 12:
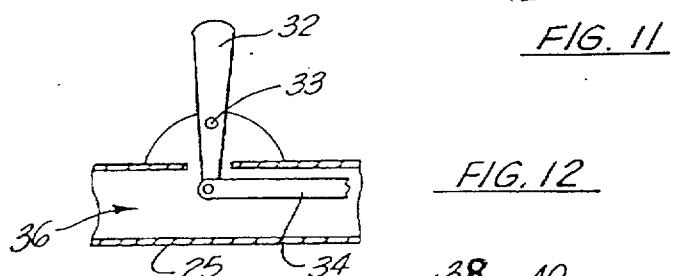
FIG. 12 is a fragmentary view of the lever portion of the preferred embodiment of the apparatus of the present invention.
Figure 13:
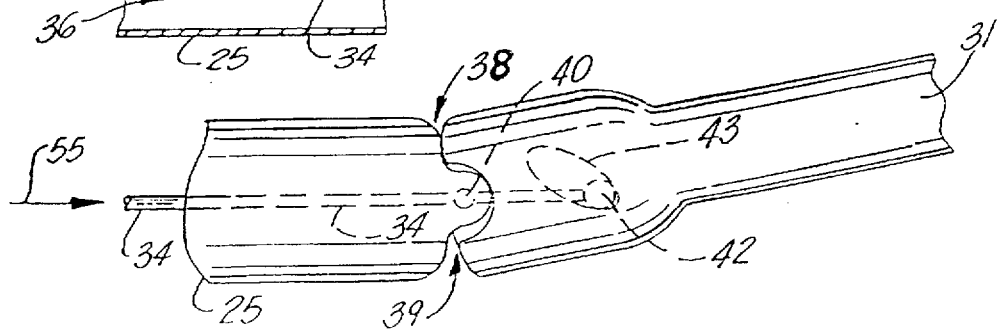
FIG. 13 is a fragmentary top view of the preferred embodiment of the apparatus of the present invention illustrating an articulation of the distal end portion of the inserter instrument.

External tubular member 25 has a proximal end 29 and a distal end 30. A grasping portion 31 is attached to the distal end 30 as shown in FIGS. 7 and 9–13. Lever 32 is pivotally attached to the proximal 29 end portion of external tubular member 25. Lever 32 is attached to pushrod 34 so that pivoting of lever 32 about its pivot 33 operates to extend or retract the pushrod relative to external tubular member 25. The lever 32 is used to articulate grasping portion 31 into multiple angular positions relative to the central longitudinal axis of the external tubular member 25 as illustrated in FIGS. 10–11 and 13.

A cable 35 is attached to internal tubular member 27. The cable 35 extends through a longitudinal bore 36 within external tubular member 25. As will be described more fully hereinafter, the cable 35 is moved by pulling or pushing the internal tubular member 27 relative to the external tubular member 25 using handles 26, 28.

An articulating joint 37 forms a connection between external tubular member 25 and grasping portion 31. As shown in FIGS. 10–11 and 13, a pair of spaces 38, 39 are provided at articulating joint 37 for allowing the grasping portion 31 to move left to right and angulate relative to the central longitudinal axis of external tubular member 25 as shown in FIGS. 10–11 and 13. A pinned connection 40 is formed at articulating joint 37 between the distal end 30 of external tubular member 25 and the grasping portion 31, allowing portion 31 to pivot upon tubular member 25.

Pushrod 34 includes an elbow section 41 that carries button 42. The button 42 fits in a recess 43. The recess 43 is formed on fixed member 44 of grasping portion 31. A moving member 45 is placed in close approximate to the fixed member 44. The moving member 45 travels away from the fixed member 44 when the cable 35 is pulled using lever 32. Cable 35 is attached at 46 to moving member 45. A coil spring 47 normally holds moving member 45 in face to face contact with fixed member 44. When the user pulls the internal tubular member 27 with handle 28, cable 35 pulls down underlying support 48 and moving member 45. A plurality of cable guides 49–51 are used to route the cable as shown in FIG. 9 to the under side of moving member 45 as shown.

Figure 9:
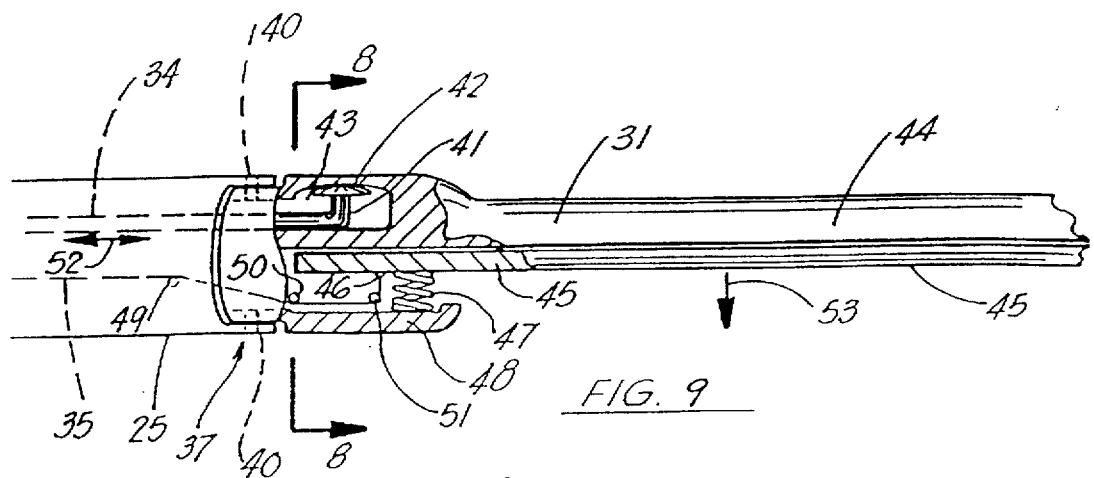
FIG. 9 is a fragmentary, partially cut-away view of the preferred embodiment of the apparatus of the present invention.

In FIG. 9, arrow 52 illustrates the movement of pushrod 34 fore and aft depending upon the surgeon's manipulation of lever 32. In FIG. 10, the pushrod 34 is a neutral position when the lever 32 is in an upright position, generally perpendicular to the central longitudinal axis of external tubular member 25 as shown in FIG. 7.

In FIG. 11, the surgeon has pulled the pushrod 34 as shown by arrow 54. This causes the button 42 to travel to the rear portion of recess 43 thereby pivoting grasping portion 31 relative to external tubular member 25. In FIG. 13, the surgeon has pushed the pushrod 34 using lever 32 as shown by the arrow 55. This causes the button 42 to travel to the forward portion of recess 43, thus pivoting the grasping portion 31 to the opposite angular position of that shown in FIG. 11. In this fashion, the surgeon can articulate or pivot the grasping portion 31 relative to the central longitudinal axis of the external tubular member 25.

In FIG. 9, arrow 53 designates a movement of moving member 45 away from fixed member 44. This is accomplished by pulling on the member 27 and its attached cable 35. Such a movement of member 45 in the direction of arrow 53 is used when either loading or releasing the sheet like member S to or from the instrument 10. The surgeon pulls the cable 35 to move member 45 away from member 44 producing a gap therebetween for application of an edge of sheet like member S thereto. In FIG. 1, the gap has been formed between members 44 and 45 so that the surgeon can insert an edge of a sheet of material S into the gap formed between the members 44 and 45.

Figure 2:
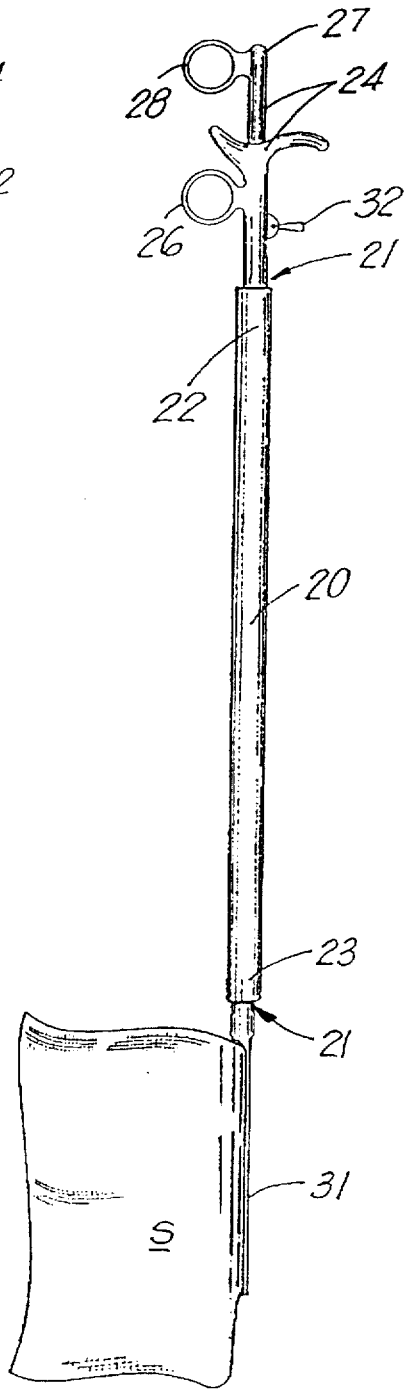
FIG. 2 is a side view of the preferred embodiment of the apparatus of the present invention illustrating the attachment of a sheet of surgical material thereto.
Figure 3:
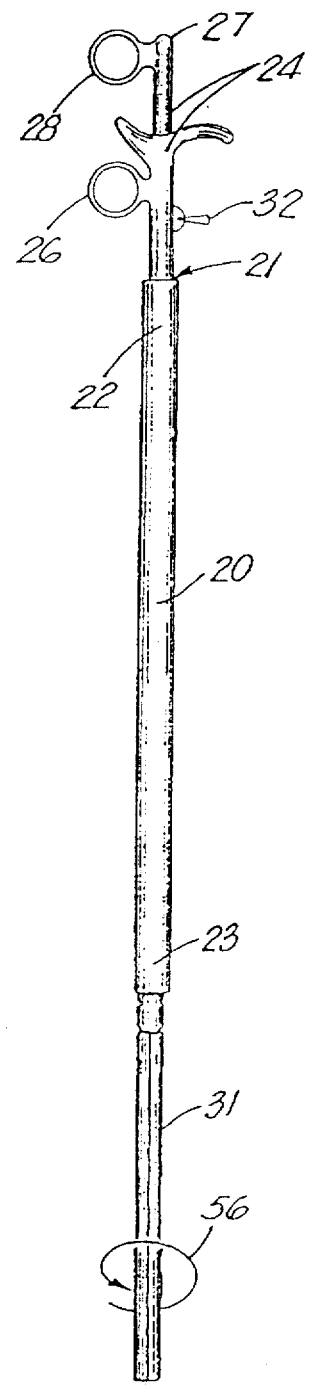
FIG. 3 is a side view of the preferred embodiment of the apparatus of the present invention showing the sheet of surgical material in a furled condition about the distal end of the inserter instrument body.

In FIG. 2, the sheet of material S has been placed in the gap between the member 44 and 45. The surgeon then releases the member 27 so that the spring 47 pushes the member 45 into close face to face contact with the member 44. This action clamps a selected edge of the sheet S between the members 44, 45 and allows the surgeon to furl the sheet S about grasping portion 31 as shown by the arrow 56 in FIG. 3.

In FIG. 4, arrow 57 indicates that the furled sheet S has been withdrawn into the bore of inserter tube 20. At this time, the sheet of material S has been furled about the grasping portion 31, and pulled into the bore 21. The combination of inserter tube 20, the sheet of material S, and the elongated inserter instrument 24 can now be inserted through tubular port member 14.

FIG. 5, the surgeon uses port 14 to place the sheet of material S into the patient's abdominal cavity 13. This is accomplished by routing the distal end 23 of inserter tube 20 and the contained inserter instrument 24 through the bore 19 of valving member 18 and then through the bore 17 of tubular port member 14. The surgeon projects the inserter tube 20 into the abdominal cavity 13 until the distal end 23 is positioned close to the distal end 16 of tubular port member 14 as shown in FIG. 5. The surgeon then holds the inserter tube 20, fixing its position relative to the tubular port 14. In the next step of the method, the surgeon forces the elongated inserter instrument 24 into the abdominal cavity by moving the elongated inserter instrument 24 relative to both inserter tube 20 and port 14 so that the grasping portion 31 and the furled sheet FS of material are exposed inside the abdominal cavity 13.

In FIG. 5, the letters FS designate the furled sheet of material having been placed with the grasping portion 31 in the patient's abdominal cavity 13. The surgeon then rotates the elongated inserter instrument 24 as indicated by the arrow 58 in FIG. 5. This rotation unfurls the sheet of material S to the position shown in FIG. 6. A second port (such as member 14) can be used for placing a grasping instrument 59 into the abdominal cavity 13 for assisting the surgeon in application of the sheet of material S as illustrated in FIG. 6.

Figure 14:
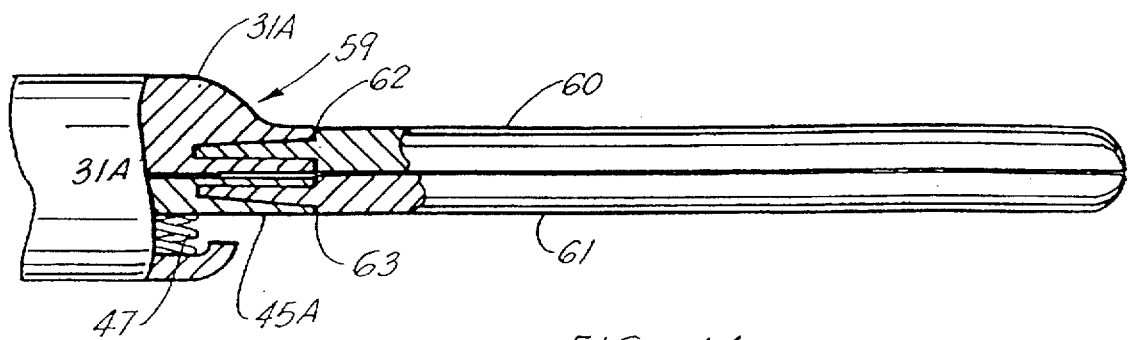
FIG. 14 is a partial, cut-away view of the distal end portion illustrating an alternative construction of the distal end portion of the inserter instrument.
Figure 15:
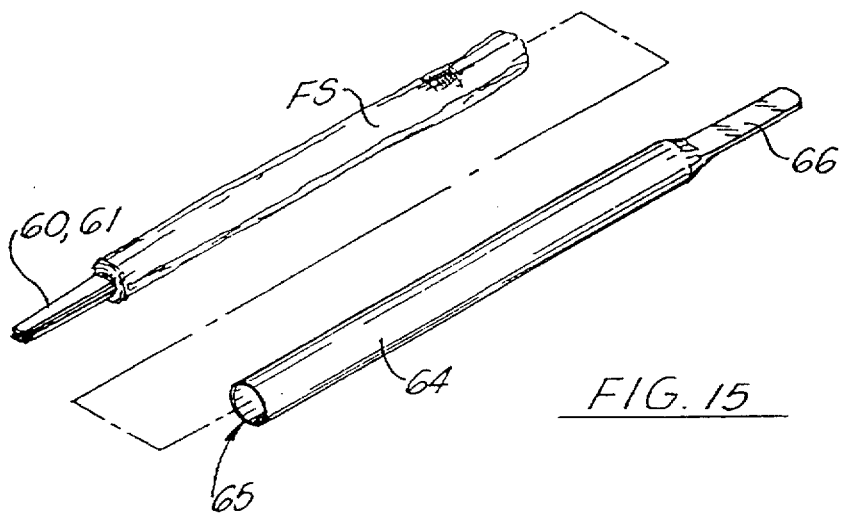
FIG. 15 is a fragmentary perspective view of the alternate construction of the distal end of the inserter instrument body.
Figure 16:
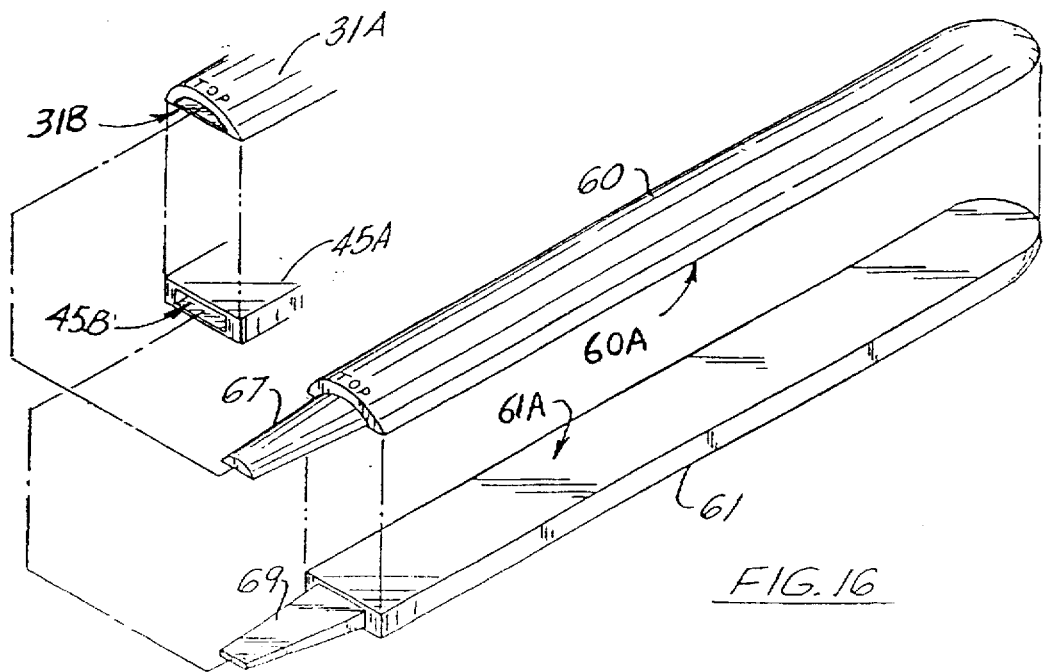
FIG. 16 is an exploded fragmentary view of the distal end portion of the inserter instrument body.

An alternate construction of the grasping portion is shown in FIGS. 14–16, designated as grasping portion 31A. Grasping portion 31A includes a removable connection designated as 60 in FIG. 14. Connection 60 is formed between grasping portion 31A and a pair of removable end 61 and grasping portion 31A. Removable end 62 is connection at joint 63B to moving member 45A.

In FIG. 15, a pre-packaged furled sheet FS of material is shown, furled about the removable ends 61, 62. The ends 61, 62 are pre-packaged with sheet S furled about the ends 61, 62. An edge of sheet S is grasped between end 61, 62. The furled sheet FS and end 62, 63 would be contained within the bore 65 of an elongated disposable sleeve 64. The sleeve 64 provides a pull tab 66 so that the user can install the furled sheet FS avoiding premature unfurling by simply holding and manipulating the sleeve 64. After the removable ends 61, 62 are installed by perfecting a connection at the joints 63A, 63B and backloading the furled sheet FS into sleeve 20, the surgeon then pulls on the pull tab 66 to remove the sleeve 64 so that the surgery can proceed.

In FIG. 16, removable end 61 provides a projection 67 that mates with a correspondingly shaped socket 68 of grasping portion 31A. Similarly, the moving member 45A provides a socket 68 that forms a connection with projecting portion 69 of end 62. The end members 61, 62 each provide correspondingly sized and shaped flat surfaces 77, 78 that abut in face to face relation when the coil spring 47 forces members 45A, and 31 and 61, 62 together.

The connection between projections 67, 69 and socket 68 and 70 can be a wedge lock or taper lock type connection to ensure a tight fit. In the embodiment of FIGS. 14–16, the removable ends 61, 62 and the furled sheet FS and sleeve 64 could be in a presterlized blister pack for example.

FIGS. 17–20 show a second alternate embodiment of the apparatus of the present invention designated generally by the numeral 70. Instrument 70 includes an external tubular member 25 that is constructed in accordance with the preferred embodiment of FIGS. 1–13. The internal member 27 is constructed generally in accordance with the preferred embodiment. However, the internal tubular member 27 carries a pushrod 71 instead of cable 35.

Pushrod 71 has a distal end in the form of a spherical member or ball 72. The member 25 has a proximal end 29 and a central longitudinal bore that accepts the internal tubular member 27. This allows the member 27 to slide within the bore of the member 25. Handle 26 and 28 enable a surgeon to grip and manipulate instrument 70 and to slide member 27 relative to member 25.

As with the preferred embodiment, the embodiment of FIGS. 17–20 includes an external tubular member 25 having a hollow bore that accepts pushrod 34. The pushrod 34 is attached to lever 32. The lever 32 affixes at pivot 33 to external tubular member 25.

In the embodiment of FIGS. 17–20, a pivotal connection 73 is formed between the member 25 and grasping portion 74. Lever 32 can be pivoted about its pivot 33 in order to extend or retract pushrod 34. As with the preferred embodiment, the pushrod 34 has an elbow section 41 and a button portion 42. As with the preferred embodiment, the button 42 occupies recess 43.

The pushrod 34 and its button 42 can be used to articulate grasping portion 74 about pivot 73 relative to external tubular member 25. This pivoting action of grasping portion 74 relative to member 25 operates the same as the pivoting that was shown and described in FIGS. 10–13 in the description of the preferred embodiment.

Figure 19:
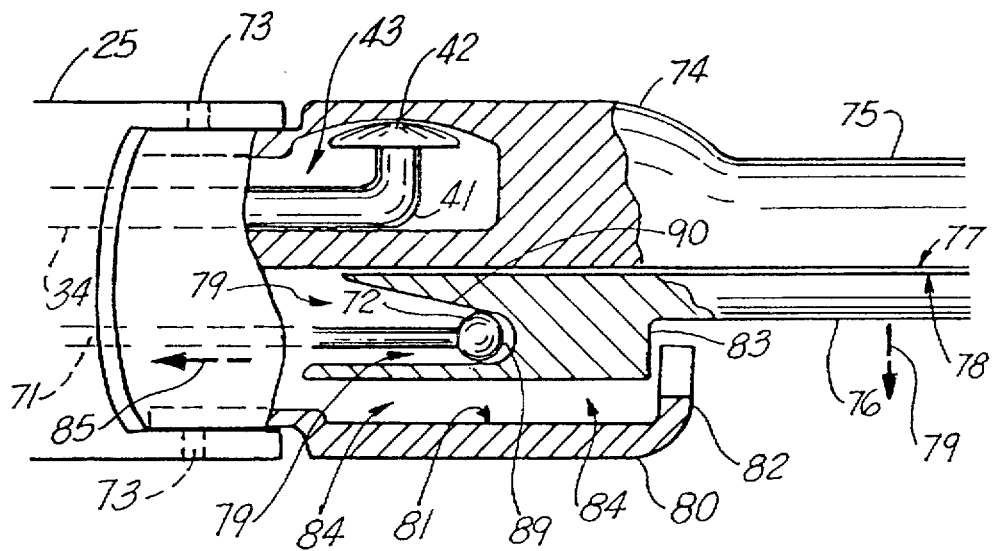
FIG. 19 is a partial, sectional elevational view of the embodiment of FIGS. 17 and 18.
Figure 20:
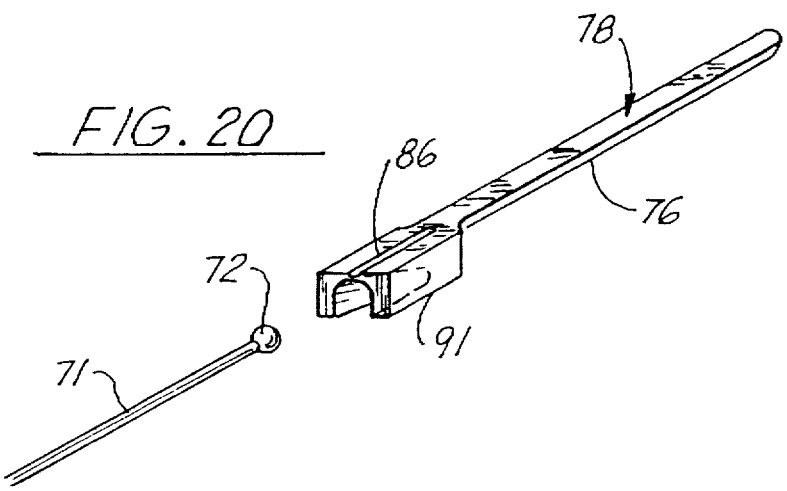
FIG. 20 is a partial perspective view of the embodiment of FIGS. 17–19.

In FIG. 19, pushrod 71 is shown having a distal end with ball 72 that fits socket 79. The socket 79 is partially cone shaped, also having a hemispherical portion 89 that registers against ball 72. Lower jaw 76 is in a closed position when ball 72 moves forward and engages the hemispherical portion 89 of socket 79. This pushes the lower jaw 76 into engagement with the upper jaw 75.

The jaw 76 has an inclined surface 90 that is engaged by the ball 72 as the pushrod 71 moves forward. Jaw 76 has a flat surface 83 that engages shoulder 82 of undersupport 80. The undersupport 80 has a flat surface 81 that receives the enlarged proximal section 91 of lower jaw 76.

In order to open the jaws 75, 76 the user pulls handle 28 of member 27. This also places pushrod 71 in tension, pulling the ball 72 away from the hemispherical portion 89 of socket 79. As ball 72 is withdrawn (see arrow 85 in FIG. 19), lower jaw 76 drops in the direction of arrow 79 due to its own weight. Shoulder 82 engages the flat surface 83 of enlarged portion 91, holding the jaw 76 in its operative position adjacent jaw 75. There is enough of a gap 84 in between the enlarged portion 91 and the undersupport 80 so that the lower jaw 76 moves away from the upper jaw 75 forming a gap therebetween to hold sheet S.

The external member 25 and jaws 75, 76 fit within the bore 21 of inserter tube 20. The member 25 is longer than tube 20 so that jaws 75, 76 can be placed inside the patient's abdominal cavity while the surgeon is holding handles 26, 28 and manipulating lever 32. This allows jaws 26, 28 to be opened and closed inside the patient's abdominal cavity. This allows the jaws 75, 76 to articulate about pivot 73. The jaws 75, 76 can be opened and closed, even when the jaws are articulated to the left or to the right of the central longitudinal axis of member 25.

As with the preferred embodiment, a sheet S of surgical material can be gripped by jaws 75, 76 and then furled about the jaws 75, 76 for entry into inserter tube 20. The jaws 75, 76 preferably present a generally cylindrically shaped outer surface when the jaws 75, 76 are closed. The inner surface of the jaws 75, 76 could be smooth for delicate materials which might break with a serrated gripper, and serrated for slipperier materials which would not break with a gripper having serrations. Serrations of various coarseness could be used (the slipperier and more tough the material to be gripped, the larger the serrations).

Figure 21:
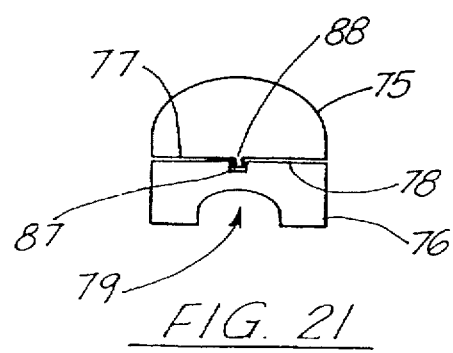
FIG. 21 is a fragmentary sectional view of the third embodiment of the apparatus of the present invention illustrating the upper and lower jaws.
Figure 22:
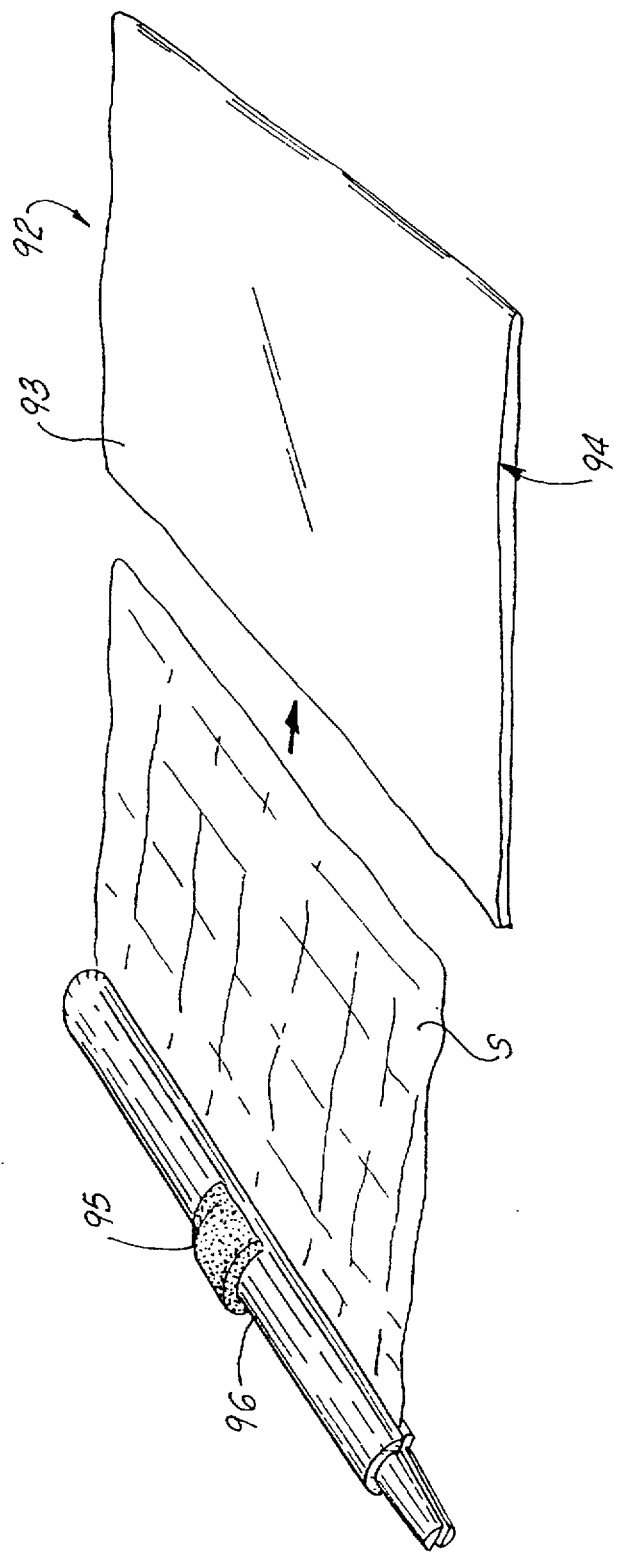
FIG. 22 is a perspective view of a fourth embodiment of the apparatus of the present invention.

In FIG. 21, a fourth embodiment of the apparatus of the present invention is shown, designated as 92 and illustrating an alternate jaw and surgical sheet arrangement and pre-packaging. To package the surgical material S with the disposable jaws 75, 76 rolling (as shown in FIG. 15) of the material S is usually easier and probably cheaper. However, rolling will generally not work well when the material S has a "memory" which might hinder unrolling during surgery, then it is preferably packaged flat in the interior 94 of envelope 93 (see FIG. 22). Plastic clip 95 shown in FIG. 22 is resilient and provides a recess 96 that conforms to the shape of the outer surface of the assembled upper jaw 75 and lower jaw 76. Plastic clip 95 holds jaws 75 and 76 together and secures the surgical sheet S in place. Plastic clip 95 pulls off after the jaws 75, 76 are snapped onto instrument in surgery as with the embodiment of FIGS. 14–16.

FIGS. 23–25 show a fifth embodiment of the apparatus of the present invention designated generally by the numeral 100. In FIGS. 23–26, a laparoscopic instrument 100 can be used to transmit gels, liquids, and like medicines to selected portions of the patient's abdominal cavity using a variety of dispensing head portions as will be discussed more fully hereinafter.

Laparoscopic instrument 100 includes an elongated main body 101 having a pushrod 102 that extends between collar 107 and control lever 103. The instrument body 101 has a proximal end 104, a distal end 105, and a pivotal connection 106 is provided between main body 101 and collar 107.

As shown in FIG. 23A, collar 107 has a hollow open ended bore 110 that communicates with a similar elongated open end cylindrical bore 111 of main body 101. The bore sections 110, 111 are sized and shaped to receive elongated cylindrically shaped dispensing member 112 in a removable fashion. The user can select a particular elongated dispensing member 112 having a selected member head portion 115–122 as shown in FIG. 1.

Dispensing member 112 is an elongated flexible conduit member such as a flexible hose. The dispensing member 112 has a proximal end 113, a distal end 114, and an open ended bore 112A that extends the full length of the dispensing member 112 so that fluids can be conveyed from the proximal 113 to the distal 114 end of dispensing member 112 and through a selected head 116–122 into the patient's abdomen.

Inner shaft 123 provides proximal end 124, distal end 125, and open ended bore 126. Inner shaft 126 is equipped with a rubber gasket seal 127 at its proximal 127 end portion. During use, inner shaft 123 is first placed inside the bore 11 of main body 101. The surgeon then selects a desired elongated flexible dispensing member 112 having a particular desired head 116–122 as selected by the surgeon.

The elongated flexible dispensing member 112 is placed inside the bore 110, 111 sections of collar 107 and main body 101. Further, inner shaft 123 is placed into instrument main body 101, bore 111 at the proximal 104 end of main body 101. Thus, in the proximal 104 region of instrument main body 101, dispensing tube 112 fits the bore 126 of inner shaft 123. The combination of dispensing member 112 and inner shaft 123 fits inside bore 111. Handles 128, 129 allow the surgeon to grip and manipulate main body 101, inner shaft 123, and the particular selected long flexible dispensing member 112.

With the present invention, a variety of flexible plastic dispensing tube members 112 can be provided. As shown in FIG. 23, theses various heads 116–122 have different designs which allow different types of liquid, gels, medicinal materials to be administered in different patterns of application. These different heads 115–122 can be used, for example to provide a pin point, broad, shower-like or other type of spray within the patient's abdomen. These tube like dispensing members 112 preferably consist of a long flexible tube member which inserts into the main body 101 through its bore 110,111.

The chosen or selected flexible plastic dispensing tube member 112 also passes through the bore 126 of inner shaft 123 which slides into main body 101, bore 111. The flexible dispensing tube 112 thus traverses the entire length of the main body 101 as well as the inner shaft 123. The handle 129 portion of inner shaft 123 will be closely positioned to the proximal 104 end of main body 101 and in close proximity to the handle 128 of main body 101.

The distal end 114 of the particular elongated flexible dispensing member 112 exits the bore 111 of main body 101 as shown in FIG. 23 wherein head 115 extends beyond the distal end of collar 107. The proximal end 113 of dispensing tube member 112 slides through a firm rubber gasket seal 127 that grips the dispensing tube member 112 at its proximal end 113 and holds it.

Gasket seal 127 also fits over the proximal 124 end of inner shaft 123 as shown in FIG. 23. The rubber gasket seal 127 forms a seal between the proximal end 124 of inner shaft 123 and the proximal end 113 of tube 112. The handles 128, 129 allow the surgeon to slide the inner shaft 123 and with it the selected flexible plastic dispensing tube member 112 back and forth (see arrow 132, FIG. 23) to reach greater or lesser depth and/or hard to reach areas within the patient's abdomen during surgery.

The collar 107 provides an articulating end portion to instrument 100 that can be moved left or right as indicated by arrows 108, 109 in FIG. 23. The articulating collar 107 can be moved left or right (or in any direction when the entire instrument 100 is turned or rotated) by moving control lever 103 to move pushrod 102. As shown in FIG. 23, the entire mechanism of lever 103, pushrod 102, pivot 106 is the same operating mechanism as the mechanism shown in FIGS. 9–13 in the preferred embodiment for pivoting the jaws relative to the instrument body in that embodiment.

The present invention thus allows additional maneuvering ability for positioning the head 115–122 as selected by the surgeon for application of a desired liquid gel or medicinal material and with a desired spray, pin point, broad shower or the like depending upon the head selected. Any chosen material, gel, liquid, medicine to be administered to the patient is applied by attaching a standard syringe to the proximal end 113 of dispensing tube 112 and dispensing the contents of the syringe into the bore of the dispensing tube member 112.

FIGS. 24 and 25 show in cross section examples of the spray patterns to be obtained by using head 119 and 121 respectively. These head portions 119–121 have an outwardly angled plurality of holes 130 and 131 to direct liquids, gels and like medicinal material as far outward as possible for the widest dispersion. The head 119 would preferably be used with liquids. The head 121 would preferably be used with gels.

The following table lists the parts numbers and parts descriptions as used herein and in the drawings attached hereto.

| PARTS LIST | |
| --- | --- |
| Part Number | Description |
| 10 | laparoscopy |
| 11 | abdominal wall |
| 12 | skin |
| 13 | abdominal cavity |
| 14 | tubular port |

PARTS LIST

| Part Number | Description |
|---|---|
| 15 | proximal end |
| 16 | distal end |
| 17 | cylindrical bore |
| 18 | valving member |
| 19 | bore |
| 20 | inserter tube |
| 21 | cylindrical bore |
| 22 | proximal end |
| 23 | distal end |
| 24 | inserter instrument |
| 25 | external tubular member |
| 26 | handle |
| 27 | internal tubular member |
| 28 | handle |
| 29 | proximal end |
| 30 | distal end |
| 31 | grasping portion |
| 31A | grasping portion |
| 32 | lever |
| 33 | pivot |
| 34 | pushrod |
| 35 | cable |
| 36 | longitudinal bore |
| 37 | articulating joint |
| 38 | space |
| 39 | space |
| 40 | pinned connection |
| 41 | elbow section |
| 42 | button |
| 43 | recess |
| 44 | fixed member |
| 45 | moving member |
| 46 | attachment |
| 47 | coil spring |
| 48 | underlying support |
| 49 | cable guide |
| 50 | cable guide |
| 51 | cable guide |
| 52 | arrow |
| 53 | arrow |
| 54 | arrow |
| 55 | arrow |
| 56 | arrow |
| 57 | arrow |
| 58 | arrow |
| 59 | grasping tool |
| 60 | removable connection |
| 61 | removable end |
| 62 | removable end |
| 63A | joint |
| 63B | joint |
| 64 | sleeve |
| 65 | cylindrical bore |
| 66 | pull tab |
| 67 | projection |
| 68 | socket |
| 69 | projection |
| 70 | instrument |
| 71 | cable |
| 72 | ball |
| 73 | pivot |
| 74 | grasping portion |
| 75 | upper jaw |
| 76 | lower jaw |
| 77 | flat surface |
| 78 | flat surface |
| 79 | socket |
| 80 | undersupport |
| 81 | flat surface |
| 82 | shoulder |
| 83 | flat surface |
| 84 | gap |
| 85 | arrow |
| 86 | arrow |
| 87 | groove |
| 88 | keyway |
| 89 | hemispherical |
| 90 | inclined surface |
| 91 | enlarged portion |
| 92 | jaw assembly |
| 93 | envelope |
| 94 | interior |
| 95 | plastic clip |
| 100 | laparoscopy instrument |
| 101 | body |
| 102 | pushrod |
| 103 | lever |
| 104 | proximal end |
| 105 | distal end |
| 106 | pivotal connection |
| 107 | annular collar |
| 108 | arrow |
| 109 | arrow |
| 110 | bore |
| 111 | bore |
| 112 | flexible dispensing tube |
| 112A | bore |
| 113 | proximal end |
| 114 | distal end |
| 115 | head |
| 116 | head |
| 117 | head |
| 118 | head |
| 119 | head |
| 120 | head |
| 121 | head |
| 122 | head |
| 123 | inner shaft |
| 124 | proximal end |
| 125 | distal end |
| 126 | bore |
| 127 | rubber gasket seal |
| 128 | handle |
| 129 | handle |
| 130 | holes |
| 131 | holes |
| 132 | arrow |
| S | sheet |
| FS | furled sheet |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A method of dispensing a liquid medicinal material into a patient's abdomen, comprising the steps of:

a) surgically forming a port through the patient's abdominal wall;

b) a placement of said port including placing a a first tubular member, having proximal and distal end portions and an elongated bore into the patient's abdomen, said proximal end having a valving member that valves gas flow through the bore and between the proximal and distal ends;

c) inserting a second tubular member into the bore of the first tubular member and through the valves the second tubular member being an instrument body with at articulating distal end portion that can be manipulated by a surgeon;

d) valving the gas flow between the patient's abdominal cavity and the proximal end of the first tubular member with the valving member;

e) placing a selected one of a plurality of available flexible dispensing tubes into the bore of the second tubular member, each tube having a distal end with a head having a nozzle for applying the liquid with a desired spray pattern wherein each of the available dispensing tubes has a different spray pattern and each is configured to removably fit the bore of the second tubular member;

f) extending the distal end of the second tubular member and nozzle of the selected dispensing tube into the patient's abdominal cavity via the first tubular member;

g) transmitting the liquid into the patient's abdomen via the nozzle; and h) articulating the instrument body distal end to flex the distal end of the second tubular member and head of the selected dispensing tube.

2. The method of claim 1 wherein the second tubular body is generally cylindrically shaped, and includes said moving distal end portion, said second tubular body having an open ended bore and further comprising the step of pivoting the distal end portion in order to flex the dispensing tube.

3. The method of claim 1 wherein the second tubular member is a flexible tube at least at the distal end portion thereof.

4. The method of claim 1 wherein there are a plurality of available dispensing tubes, each having a distal head with a nozzle end portion having a nozzle spray pattern, and in step "f" a surgeon selects a delivery tube from the plurality of dispensing tubes.

5. The method of claim 1 wherein the second tubular member has a nozzle with a plurality of openings therethrough.

6. The method of claim 1 wherein each dispensing tube is longer than the instrument body and further comprising the step of sliding the dispensing tube relative to the instrument body during a positioning of the nozzle relative to a desired location within the abdominal cavity.

7. The method of claim 1 wherein the instrument body has an actuator at its proximal end for enabling a surgeon to manipulate the distal end thereof and further comprising the step of moving the distal end of the dispensing tube by manipulating the actuator.

8. The method of claim 7 wherein the actuator is operable by the surgeon when the nozzle is inside the patient's body cavity.

9. A method of dispensing a liquid medicinal material into the patient's abdomen, comprising the steps of:

a) surgically forming a port through the patient's abdominal wall;

b) a placement of said port including placing a first tubular member, having proximal and distal end portions and an elongated bore into the patient's abdomen, said proximal end having a valving member that valves the flow of gases through the bore and between the proximal and distal ends;

c) inserting a second tubular member into the bore of the first tubular member, and through the valve the second tubular member being an instrument body with a moving distal end portion that can be manipulated by the surgeon;

d) valving the flow of gases between the patient's abdominal cavity at the proximal end of the first tubular member with the valving member;

e) extending the distal end of the second tubular member into the patient's abdominal cavity;

f) placing a flexible dispensing tube into the bore of the second tubular member, the second tubular member having a distal end with a nozzle for applying the liquid with a desired spray pattern;

g) transmitting the liquid into the patient's abdomen via the nozzle;

h) articulating the instrument body distal end to flex the distal end of the dispensing tube; and i) the second tubular member has a pivot at the distal end portion thereof, and in step "h", the distal end of the second tubular member is pivoted during articulating of the instrument body and the dispensing tube.

10. A surgical endoscopic instrument for dispensing fluids through a surgically formed port in a patient's body cavity wall comprising;

a) a tube that can be surgically placed by a surgeon through a surgical opening in a patient's body cavity wall, said tube having a bore with a central longitudinal axis;

b) an instrument body that can be placed in the bore of the tube, and having proximal and distal end portions and an instrument body bore;

c) a dispensing tube that has proximal and distal end portions, the tube being sized and shaped to fit the instrument body bore and, being flexible at least at the distal end portion thereof;

d) a nozzle at the distal end of the dispensing tube for dispensing liquids, gels, and like medicinal materials into a patient's body cavity;

e) the distal end of the instrument body articulating into positions spaced away from the central longitudinal axis so that the contained flexible distal end portion of the dispensing tube also moves therewith;

f) a dispensing tube bore for for transmitting fluid between the proximal and distal end portions of the dispensing tube when the tube occupies the bore of the instrument body and the nozzle is positioned within the patient's body cavity.

11. The surgical endoscopic instrument of claim 10 wherein the dispensing tube is slidably mounted within the instrument body bore.

12. The surgical endoscopic instrument of claim 10 wherein the nozzle has a plurality of openings.

13. The surgical endoscopic instrument of claim 12 wherein the nozzle has an array of openings.

14. The surgical endoscopic instrument of claim 10 wherein there are a plurality of flexible dispensing tubes, each being sized and shaped to fit the instrument body bore, each having a nozzle with a selected spray pattern so that a surgeon can select a desired spray pattern by selecting a particular dispensing tube and inserting said selected tube into the instrument body bore.

15. The surgical endoscopic instrument of claim 10 wherein the instrument body is generally cylindrically shaped.

16. The surgical endoscopic instrument of claim 10 wherein the dispensing tube is of a flexible rubber-like material.

17. A laparoscopy instrument comprising;

a) a laparoscopy tube that can be surgically placed by a surgeon through a surgical opening in a patient's abdominal wall, said tube having a bore.

b) an instrument body that can be placed in the bore of the laparoscopy tube, and having proximal and distal end portions and an instrument body bore;

c) a flexible dispensing tube that has proximal and distal end portions, the tube being sized and shaped to fit the instrument body bore and flexible at least at the distal end portion thereof;

d) a nozzle at the distal end of the dispensing tube for dispensing liquids, gels, and like medicinal materials into a patient's abdominal cavity;

e) means for moving the distal end of the instrument body into multiple positions so that the contained flexible distal end portion of the dispensing tube also moves therewith;

f) means for transmitting fluid between the proximal and distal end portions of the dispensing tube when the tube occupies the bore of the instrument body and the nozzle is positioned within the patient's abdominal cavity; and g) the instrument body has a pivot and the distal end portion of the instrument body pivots relative to the proximal end of the instrument body.

18. A laparoscopy instrument comprising;

a) a laparoscopy tube that can be surgically placed by a surgeon through a surgical opening in a patient's abdominal wall, said tube having a bore;

b) an instrument body that can be placed in the bore of the laparoscopy tube, and having proximal and distal end portions and an instrument body bore;

c) a flexible dispensing tube that has proximal and distal end portions, the tube being sized and shaped to fit the instrument body bore and flexible at least at the distal end portion thereof;

d) a nozzle at the distal end of the dispensing tube for dispensing liquids, gels, and like medicinal materials into a patient's abdominal cavity;

e) means for moving the distal end of the instrument body into multiple positions so that the contained flexible distal end portion of the dispensing tube also moves therewith;

f) means for transmitting fluid between the proximal and distal end Portions of the dispensing tube when the tube occupies the bore of the instrument body and the nozzle is positioned within the patient's abdominal cavity; and g) the instrument body has an open ended bore that extends from the proximal end, through the moving means to the distal end.

19. A laparoscopy instrument comprising;

a) a laparoscopy tube that can be surgically placed by a surgeon through a surgical opening in a patient's abdominal wall, said tube having a bore;

b) an instrument body that can be placed in the bore of the laparoscopy tube, and having proximal and distal end portions and an instrument body bore;

c) a flexible dispensing tube that has proximal and distal end portions, the tube being sized and shaped to fit the instrument body bore and flexible at least at the distal end portion thereof;

d) a nozzle at the distal end of the dispensing tube for dispensing liquids, gels, and like medicinal materials into a patient's abdominal cavity;

e) means for moving the distal end of the instrument body into multiple positions so that the contained flexible distal end portion of the dispensing tube also moves therewith;

f) means for transmitting fluid between the proximal and distal end portions of the dispensing tube when the tube occupies the bore of the instrument body and the nozzle is positioned within the patient's abdominal cavity; and g) the instrument body comprises a pair of body sections including a smaller distal section and a larger proximal section.

20. The surgical endoscopic instrument of claim 19 wherein each of the sections has a bore.

* * * * *